United States Patent [19]
Laugier et al.

[11] Patent Number: 5,560,904
[45] Date of Patent: Oct. 1, 1996

[54] COSMETIC AND/OR DERMATOLOGICAL COMPOSITION CONTAINING A GLYCERYL TRI(α-HYDROXYACYLATE) AS SOLE PRECURSOR OF GLYCEROL

[75] Inventors: Jean-Pierre Laugier, Antony; Jean-Francois Nadaud, Clamart, both of France

[73] Assignee: L'Oreal, Paris, France

[21] Appl. No.: 421,390

[22] Filed: Apr. 13, 1995

[30] Foreign Application Priority Data

Apr. 18, 1994 [FR] France ................................. 94 04602

[51] Int. Cl.⁶ .................................................. A61K 31/74
[52] U.S. Cl. .................. 424/78.08; 514/844; 514/846; 514/847; 525/408; 525/413; 525/415; 528/354; 528/361
[58] Field of Search ................... 424/78.08; 514/844, 514/846, 847; 525/408, 413, 415; 528/354, 361

[56] References Cited

U.S. PATENT DOCUMENTS 4,675,177  6/1987  Geary et al. .
4,760,096  7/1988  Sakai et al. .

FOREIGN PATENT DOCUMENTS 2092444  6/1982  United Kingdom .

*Primary Examiner*—James J. Seidleck
*Assistant Examiner*—Terressa M. Mosley
*Attorney, Agent, or Firm*—Oblon, Spivak, McClelland, Maier & Neustadt, P.C.

[57] ABSTRACT

Use of a glyceryl tri(α-hydroxyacylate) in a cosmetic and/or dermatological composition as the sole precursor of glycerol and of hydroxy acid, which is capable of releasing the glycerol and the hydroxy acid onto the skin via an enzymatic reaction, in order to moisturize and soften the skin. Useful especially for moisturizing and/or treating dry skin.

10 Claims, No Drawings

COSMETIC AND/OR DERMATOLOGICAL COMPOSITION CONTAINING A GLYCERYL TRI(α-HYDROXYACYLATE) AS SOLE PRECURSOR OF GLYCEROL

FIELD OF THE INVENTION

The present invention relates to the use of a glyceryl tri(α-hydroxyacylate) in a cosmetic and/or dermatological composition for moisturizing and/or softening the skin, both of the face and of the body, including the scalp and around the eyes. The invention also relates to a cosmetic and/or dermatological treatment process via the topical route, for moisturizing and/or softening the skin.

BACKGROUND OF THE INVENTION

Skin has a tendency to become dry upon exposure to air and sun; the loss of water at the skin surface also results in a loss of water in the *stratum corneum*. For this reason, it is important for the skin to be well moisturized and not to suffer a loss of water which withers skin, and thus causes its premature ageing, drying and even desquamation. Thus, in the cosmetics field, it is common to incorporate into compositions used as moisturizing agents hygroscopic substances which bring about a rehydration of the skin by uptake of atmospheric water and by retention of the water in the skin.

Among the many moisturizing agents, the most commonly used are polyols, and especially glycerol which is a water trap on account of its hydroxyl groups; one molecule of glycerol takes up six molecules of water. Furthermore, glycerol is not very bulky, enabling it to penetrate into the skin. See the paragraph on glycerine in *The Principles and Practice of Modern Cosmetics* by R. G. Harry, 1963, Volume II pages 202 to 205 incorporated herein by reference. The only drawback with glycerol is that it gives a sticky nature to compositions which contain large amounts of it.

It is also known to use hydroxy acids and salts thereof, and especially lactic acid and sodium lactate, the latter being one of the components of the NMF (Natural Moisturizing Factor) present in the skin; indeed, it is thought that lactic acid or the salt thereof modifies the spatial conformation of the proteins in the stratum corneum. As a result, it improves the suppleness and the elasticity of the skin. See the article by M. Rieger, *Cosmetics & Toiletries*, 1992, Vol. 107, pp. 89–90 incorporated herein by reference. Unfortunately, hydroxy acids and salts thereof have the drawback of being difficult to incorporate into a cosmetic and/or dermatological composition, especially when it is desired to use them in large amounts, because they are then incompatible with most of the gelling agents usually used to stabilize such compositions. This incompatibility is reflected in the destabilization of compositions which contain them. In the case of an emulsion, a separation of the aqueous and oily phases takes place, and in the case of a gel, it breaks.

In order to overcome this problem, it is possible either to incorporate hydroxy acids and salts thereof in very small amounts, or to use them in very specific vehicles which are compatible, which, in both cases, limits the freedom of formulation. Thus, lactic acid or sodium lactate are still used with the same types of gelling agent and of emulsifying agent, and compositions of the same texture, usually greasy and waxy, are thus still obtained. It is thus very difficult to use hydroxy acids and salts thereof in just any type of composition. In particular, it is not possible to obtain milks and lotions.

OBJECTS OF THE INVENTION

One object of the present invention is a cosmetic and/or dermatological composition which makes it possible to overcome the above-mentioned problems.

DETAILED DESCRIPTION OF THE PREFERRED EMBODIMENTS

The inventors have discovered, surprisingly, that the use of a glyceryl tri(α-hydroxyacylate) in a cosmetic and/or dermatological composition makes it possible to obtain at least the same effects on the skin as those obtained with glycerol and the corresponding hydroxy acid of this glyceryl tri(α-hydroxyacylate), while at the same time allowing the use of any type of gelling agent and emulsifying agent, and thus making it possible to obtain new dosage forms which were heretofore impossible to stabilize in the presence of hydroxy acids and/or hydroxy acid salts, such as aqueous gels and fluid emulsions.

The glyceryl tri(α-hydroxyacylates) of the invention have the additional advantage of being easy to introduce into cosmetic and/or dermatological compositions, and of providing less sticky compositions than those which contain an equivalent amount of glycerol. In particular, glyceryl tri(α-hydroxyacylates) are less hydrophilic than hydroxy acids generally and react less with the constituents of the composition containing them.

One subject of the present invention is thus the use of a glyceryl tri(α-hydroxyacylate) in a cosmetic and/or dermatological composition as sole precursor of both glycerol and of a hydroxy acid, which is capable of releasing the glycerol and the hydroxy acid onto the skin via an enzymatic reaction, in order to moisturize and/or soften the skin. The compositions also make up part of the invention.

The term precursor as used herein refers to a compound which, on contact with the stratum corneum, is hydrolysed by the action of a specific enzyme therein and releases a free active agent. A precursor generally has the drawback of being less efficient than the free active agent. However, in the case of glyceryl trilactate, surprisingly, the moisturizing efficiency is identical to, or even greater than, that of the released active agents.

Generally, according to the present invention only one precursor is used. It is, however, possible to combine therewith other active agents which are not found in the form of bioconvertible precursors on the skin.

Examples of the glyceryl tri(α-hydroxyacylate) of the invention include a compound of formula:

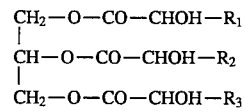

where $R_1$, $R_2$ and $R_3$ are the same or different and each represents the radical $C_nH_{2n+1}$, n being an integer of from 0 to 12.

Preferred glyceryl tri(α-hydroxyacylates) include glyceryl trilactate, glyceryl triglycolate, glyceryl trimandelate, glyceryl tritartrate and glyceryl tricitrate. The compositions according to the present invention and containing a glyceryl tri(α-hydroxyacylate) make it possible to combat the dehydration and drying of the skin and consequently to combat its ageing. The cosmetic treatment process for moisturizing and/or softening the skin according to the invention thus comprises applying to the skin a composition containing a glyceryl tri(α-hydroxyacylate). A further subject of the present invention is the use of a glyceryl tri(α-hydroxyacylate) for the preparation of cosmetic and/or dermatological compositions for treating dry skin and these compositions themselves. The compositions according to the invention may contain, for example, from 0.01 to 20% by weight of glyceryl tri(α-hydroxyacylate) relative to the total weight of the composition, preferably from 0.5 to 10% by weight but including all values and all ranges therebetween.

The composition according to the invention may be provided in all the dosage forms normally used for a topical application and, for example, in the form of an aqueous or aqueous-alcoholic lotion, in the form of an aqueous gel, in the form of a serum, or in the form of an oil-in-water (O/W) or water-in-oil (W/O) emulsion. It may also be in the form of spherules such as lipid vesicles which are ionic (liposomes) or nonionic, nanocapsules and nanospheres. In particular, the emulsions may be in the form of milks which are fluid emulsions. In practice, a fluid emulsion generally preferably has a viscosity below 8 poises (0.8 Pa.s), measured on a Contraves MTV viscometer, meaning that it flows under its own weight. It is also particularly advantageous to be able to obtain aqueous gels containing little or no oil. Any type of gelling agent may be used to do this and, for example, a carboxyvinyl polymer (carbomer), an acrylic copolymer such as acrylate/alkylacrylate copolymers, a polyacrylamide or a polysaccharide may be used.

When the invention composition is an emulsion, the proportion of the fatty (hydrophobic) phase may range from 5% to 80% by weight, preferably from 5% to 50% by weight but including all values and all ranges therebetween, relative to the total weight of the composition. The oils, the emulsifying agents and co-emulsifying agents used in the composition in emulsion form are chosen from those conventionally used in the cosmetics field. The emulsifying agent and the co-emulsifying agent are then present, in the composition, in a proportion ranging from 0.3% to 30% by weight, and preferably from 0.5% to 30% by weight, relative to the total weight of the composition. The emulsion may additionally contain lipid vesicles.

The cosmetic and/or dermatological compositions of the invention may also contain adjuvants which are common in the cosmetics and/or dermatological field, such as hydrophilic or lipophilic gelling agents, hydrophilic or lipophilic active agents, preserving agents, antioxidants, fragrances, fillers, screening agents and dyes. The amounts of these various adjuvants are those conventionally used in the cosmetics and/or dermatological field and, for example, are from 0.01% to 10% of the total weight of the composition. Depending on their nature, these adjuvants may be introduced into one or more of the fatty phase, the aqueous phase and/or the lipid spherules.

Oils which may be used in the invention include mineral oils (e.g., liquid petrolatum), plant oils (e.g., sunflower oil), synthetic oils (e.g., isopropyl myristate, perhydrosqualene, lanolin or purcellin oil), silicone-containing oils (e.g., cyclomethicone) and fluorine-containing oils (e.g., perfluoro polyethers). Fatty alcohols and fatty acids (e.g., cetyl alcohol, stearic acid and lanolin alcohol) may be added to these oils.

Examples of W/O emulsifying agents which may be used in the invention include the mixture of polyglyceryl-4 isostearate/cetyldimethicone copolyol/hexyl laurate sold under the name ABIL WE 09 by Goldschmidt and the mixture mineral oil/petrolatum/ozokerite/glyceryl oleate/lanolin alcohol sold under the name PROTEGIN X by Goldschmidt.

O/W emulsifying agents which may be used in the invention include the mixture glyceryl stearate/PEG-100 stearate sold under the name ARLACEL 165 by ICI, polysorbate-60 sold under the name TWEEN 60 by ICI, PEG-400, glyceryl stearate, the mixture PEG-6/PEG-32/glycol stearate sold under the name TEFOSE 63 by Gattefosse, and the mixture PEG-100 stearate/glyceryl stearate sold under the name SIMULSOL 165 by Seppic.

Examples of hydrophilic gelling agents include those indicated above as well as natural gums and clays, and, as lipophilic gelling agents, examples include modified clays such as bentones, fatty acid metal salts such as aluminum stearates, and hydrophobic silica. Hydrophilic active agents which may be used herein include proteins or protein hydrolysates, amino acids, polyols, urea, allantoin, sugars and sugar derivatives, vitamins, hydroxy acids, etc. Lipophilic active agents which may be used herein include retinol (vitamin A) and derivatives thereof, tocopherol (vitamin E) and derivatives thereof, essential fatty acids, ceramides, essential oils, salicylic acid and derivatives thereof, etc. UV screening agents having a lipophilic or hydrophilic property, titanium oxide and zinc oxide may also be used in the composition according to the invention.

EXAMPLES

The tests which follow show the results obtained for moisturization with glyceryl trilactate compared with glycerol and with sodium lactate. The moisturization was measured, on the one hand, with a corneometer which measures the capacitance of the skin in vivo, and, on the other hand, with a dermodiag which measures the conductance of the skin in vivo. The two measurements complement each other to reflect the moisturization of a substance.

The results are collated in the table below, in which the percentages shown represent the increase in capacitance or in conductance relative to those found for naked skin:

|  | Excipient | 5% Glycerol | 5% Glyceryl trilactate | 3% Sodium lactate |
|---|---|---|---|---|
| Corneometer | +9% | +22% | +22% | +23% |
| Dermodiag | +10% | +25% | +20% | +5% |

5% of glyceryl trilactate corresponds to 1.25% of glycerol and 3.75% of lactate, and 3% of sodium lactate corresponds to about 2.7% of lactate.

The results presented in the above table show that glyceryl trilactate provides an overall moisturization equivalent to that of a four-times greater amount of glycerol and is more advantageous than a corresponding amount of lactate.

| Example 1: Emulsion of O/W type | |
|---|---|
| Phase A: | |
| Cyclomethicone | 10 g |
| Perhydrosqualene | 18 g |
| Liquid petrolatum | 5 g |
| Liquid lanolin | 4 g |
| Glyceryl stearate/PEG-100 stearate (Arlacel ® 165 from ICI) | 6 g |
| Polysorbate 60 (Tween ® 60 from ICI) | 2 g |
| Cetyl alcohol | 1.2 g |
| Stearic acid | 2.5 g |
| Tocopherol Acetate (antioxidant) | 0.3 g |
| Phase B: | |
| Triethanolamine | 0.1 g |
| Preserving agent (methylparaben) | 0.3 g |
| Glyceryl trilactate | 5 g |
| Demineralized water | qs 100 g |

Procedure

Phase A is heated to 75° C. Phase B is similarly heated and Phase A is poured into Phase B with stirring. The mixture is cooled to room temperature. A smooth moisturizing care cream which is typical of those used during the day is obtained.

| Example 2: Emulsion of O/W type | |
|---|---|
| Phase A: | |
| Fragrance | 0.5 g |
| Carbomer | 0.2 g |
| Isopropyl myristate | 1 g |
| Cetyl alcohol | 3 g |
| Stearic acid | 3 g |
| Glyceryl stearate | 3 g |
| Corn oil | 2 g |
| Phase B: | |
| Glyceryl trilactate | 5 g |
| Propylene glycol | 2 g |
| PEG-400 | 3 g |
| Preserving agent (methylparaben) | 0.3 g |
| Demineralized water | qs 100 g |

The process is performed as in Example 1. A moisturizing care cream as in Example 1 is obtained.

| Example 3: Emulsion of W/O type | |
|---|---|
| Phase A: | |
| Mineral oil/petrolatum/ozokerite/glyceryl oleate/lanolin alcohol (Protegin X from Goldschmidt) | 20 g |
| Liquid petrolatum | 10 g |
| Fragrance | 1 g |
| Sunflower oil | 15 g |
| Phase B: | |
| Preserving agent (methylparaben) | 0.3 g |
| Glycerol | 5 g |
| Magnesium sulphate | 0.5 g |
| Glyceryl trilactate | 5 g |
| Demineralized water | qs 100 g |

Procedure

Phases A and B are heated separately to 75° C. Phase B is then poured into Phase A. A nourishing cream having good moisturizing properties, which is typical of those used at night, is obtained.

| Example 4: Emulsion of W/O type | |
|---|---|
| Phase A: | |
| Polyglyceryl-4 isostearate/cetyldimethicone copolyol/hexyl laurate (Abil WE 09 from Goldschmidt) | 5 g |
| Isopropyl myristate | 5 g |
| Cyclomethicone | 8 g |
| Liquid petrolatum | 5 g |
| Silica (Aerosil ® 200 from Degussa) | 0.4 g |
| Purcellin oil (sold by the company Société Stéarineries Dubois) | 14 g |
| Phase B: | |
| Sodium chloride | 0.5 g |
| Preserving agent | 0.3 g |
| Glyceryl trilactate | 5 g |
| Demineralized water | qs 100 g |

The process is performed as in the above example and a moisturizing night cream is obtained.

| Example 5: Aqueous-alcoholic gel | |
|---|---|
| Carbomer | 0.9 g |
| Ethyl alcohol | 10 g |
| Triethanolamine | 0.3 g |
| Fragrance | 0.3 g |
| Preserving agent (methylparaben) | 0.3 g |
| Glyceryl trilactate | 5 g |
| Demineralized water | qs 100 g |

A moisturizing tonic to be used for cleaning the skin is obtained.

| Example 6: O/W emulsified gel | |
|---|---|
| Phase A: | |
| Cyclomethicone | 3 g |
| Purcellin oil (sold by the company Dragocco) | 7 g |
| PEG-6/PEG-32/glycol stearate (Tefose ® 63 from Gattefosse) | 0.3 g |
| Fragrance | 0.4 g |
| Phase B: | |
| Carbomer | 0.6 g |
| Ethyl alcohol | 10 g |
| Triethanolamine | 0.2 g |
| Glyceryl trilactate | 5 g |
| Methylparaben (preserving agent) | 0.3 g |
| Demineralized water | qs 100 g |

For the preparation, the process is performed as in Example 1, heating phases A and B to 60° C. and 40° C. respectively. A gel which may be used for moisturizing and cleaning the skin is obtained.

| Example 7: Gel | |
|---|---|
| Carbomer | 0.6 g |
| Triethanolamine | 0.3 g |
| Preserving agent (methylparaben) | 0.3 g |
| Propylene glycol | 3 g |
| Glyceryl trilactate | 5 g |
| Demineralized water | qs 100 g |

A moisturizing gel suitable for sensitive skins is obtained.

| Example 8: Cream containing nonionic vesicles | |
|---|---|
| Phase A: | |
| Polyglyceryl-3 cetyl ether | 3.8 g |
| β-Sitosterol | 3.8 g |
| Dicetyl phosphate | 0.4 g |
| Phase B: | |
| Preserving agent | 0.3 g |
| Sunflower oil | 35 g |
| Fragrance | 0.6 g |
| Phase C: | |
| Carbomer | 0.2 g |
| Triethanolamine | 0.2 g |
| Glyceryl trilactate | 5 g |
| Demineralized water | qs 100 g |

Procedure

The constituents of Phase A are melted at 100° C., water is added thereto with stirring and the mixture is passed twice through a homogenizer, at high pressure, in order to form the vesicles.

The constituents of Phase B are heated at 70° C. until they have completely dissolved. The mixture is cooled and Phase B is added to Phase A.

After passing twice through a homogenizer at high pressure, the mixture is cooled and Phase C is added with stirring.

A nourishing and moisturizing cream is obtained.

Example 9: Emulsion of O/W type

Phase A:

| | |
|---|---|
| Cyclomethicone | 5 g |
| Lanolin alcohol | 1.5 g |
| Liquid petrolatum | 10 g |
| PEG-100 stearate/glyceryl stearate (Simulsol ® 165 from Seppic) | 2.1 g |
| Polysorbate-60 (Tween ® 60 from ICI) | 0.9 g |
| Cetyl alcohol | 0.5 g |
| Stearic acid | 0.72 g |

Phase B:

| | |
|---|---|
| Carbomer | 0.2 g |
| Xanthan gum | 0.1 g |
| Triethanolamine | 0.45 g |
| Preserving agent (methylparaben) | 1.16 g |
| Glyceryl trilactate | 5 g |
| Demineralized water | qs 100 g |

The process is performed as in Example 1 and a cream comparable to that of Example 1 is obtained.

Example 10: Emulsion of O/W type

Phase A:

| | |
|---|---|
| Cyclomethicone | 10 g |
| Lanolin alcohol | 1.5 g |
| Liquid petrolatum | 5 g |
| PEG-100 stearate/glyceryl stearate (Simulsol ® 165 from Seppic) | 21 g |
| Polysorbate-60 (Tween ® 60 from ICI) | 0.9 g |
| Cetyl alcohol | 0.5 g |
| Stearic acid | 0.72 g |

Phase B:

| | |
|---|---|
| Carbomer | 0.2 g |
| Xanthan gum | 0.1 g |
| Triethanolamine | 0.45 g |
| Glycerine | 3 g |
| Preserving agent (methylparaben) | 1.1 g |
| Glyceryl trilactate | 2 g |
| Demineralized water | qs 100 g |

The preparation and the cream obtained are identical to those of Example 1.

This application is based on France 94-04602, filed Apr. 18, 1994, incorporated herein by reference.

What is claimed as new and desired to be secured by Letters Patent of the United States is:

1. A composition comprising one or more glyceryl tri(α-hydroxyacylates) in a cosmetic and/or dermatological carrier as sole precursor of glycerol and of hydroxy acid, said composition capable of releasing glycerol and hydroxy acid onto the skin via an enzymatic reaction, said glyceryl tri(α-hydroxyacylates) being present in the composition in an effective amount to moisturize and/or soften the skin, wherein said one or more glyceryl tri(α-hydroxyacylates) is a compound of the formula;

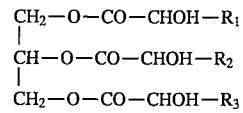

where $R_1$, $R_2$ and $R_3$ are the same or different and each represents the radical $C_nH_{2n+1}$, n being an integer of from 0 to 12.

2. The composition according to claim 1, characterized in that the one or more glyceryl tri(α-hydroxyacylates) is one or more selected from the group consisting of glyceryl trilactate, glyceryl triglycolate, glyceryl trimandelate, glyceryl tritartrate and glyceryl tricitrate.

3. The composition according claim 1, characterized in that the one or more glyceryl tri(α-hydroxyacylates) is glyceryl trilactate.

4. The composition according to claim 1, characterized in that the composition comprises from 0.01 to 20% by weight of said one or more glyceryl tri(α-hydroxyacylates) relative to the total weight of the composition.

5. The composition according to claim 1 characterized in that the composition comprises from 0.5 to 10% by weight of said one or more glyceryl tri(α-hydroxyacylates) relative to the total weight of the composition.

6. The composition according to claim 1, characterized in that the composition is in the form of an aqueous gel.

7. The composition according to claim 1 characterized in that the composition is in the form of a fluid emulsion.

8. A process for moisturizing and/or softening the skin, comprising applying to the skin an effective amount of a composition comprising one or more glyceryl tri (α-hydroxyacylates), wherein said one or more glyceryl tri (α-hydroxyacylates) is a compound of the formula:

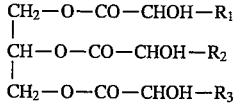

where $R_1$, $R_2$ and $R_3$ are the same or different and each represents the radical $C_nH_{2n+1}$, n being an integer from 0 to 12.

9. The process according to claim 8 characterized in that the one or more glyceryl tri(α-hydroxyacylates) is one or more selected from glyceryl trilactate, glyceryl triglycolate, glyceryl trimandelate, glyceryl tritartrate and glyceryl tricitrate.

10. The process for moisturizing and softening the skin as claimed in claim 8, comprising applying to the skin a composition containing glyceryl trilactate.

* * * * *